(12) United States Patent
Vaillancourt et al.

(10) Patent No.: US 12,133,959 B2
(45) Date of Patent: Nov. 5, 2024

(54) DRESSING

(71) Applicants: Michael J. Vaillancourt, Chester, NJ (US); Marshall Kerr, Oceanside, CA (US); Michael Pfefferkorn, Succasunna, NJ (US)

(72) Inventors: Michael J. Vaillancourt, Chester, NJ (US); Marshall Kerr, Oceanside, CA (US); Michael Pfefferkorn, Succasunna, NJ (US)

(73) Assignee: VLV ASSOCIATES, INC., Whippany, NJ (US)

( * ) Notice: Subject to any disclaimer, the term of this patent is extended or adjusted under 35 U.S.C. 154(b) by 857 days.

(21) Appl. No.: 16/991,747

(22) Filed: Aug. 12, 2020

(65) Prior Publication Data
US 2020/0368498 A1 Nov. 26, 2020

Related U.S. Application Data

(63) Continuation of application No. 15/193,681, filed on Jun. 27, 2016, now Pat. No. 10,835,717.

(51) Int. Cl.
*A61M 25/02* (2006.01)
(52) U.S. Cl.
CPC ..... *A61M 25/02* (2013.01); *A61M 2025/0246* (2013.01); *A61M 2025/0253* (2013.01); *A61M 2025/0266* (2013.01); *A61M 2025/0273* (2013.01)
(58) Field of Classification Search
CPC .......... A61M 25/02; A61M 2025/0273; A61M 2209/088; A61M 25/002; A61M 2025/0246; A61M 2025/0266; A61M 2005/1586; A61F 13/00; A61F 13/0259; A61F 13/00029; A61F 13/02; A61F 13/0253; A61F 13/84; A61F 2013/00182; A61F 2013/0057
See application file for complete search history.

(56) References Cited

U.S. PATENT DOCUMENTS

| | | | | |
|---|---|---|---|---|
| 3,782,377 | A * | 1/1974 | Rychlik | A61M 25/02 128/DIG. 6 |
| 3,834,380 | A * | 9/1974 | Boyd | A61M 25/02 128/DIG. 26 |
| 3,900,026 | A * | 8/1975 | Wagner | A61M 25/02 604/174 |
| 3,918,446 | A * | 11/1975 | Buttaravoli | A61M 25/02 128/DIG. 26 |

(Continued)

OTHER PUBLICATIONS

"Dressing." Merriam-Webster.com Dictionary, Merriam-Webster, https://www.merriam-webster.com/dictionary/dressing. Accessed Oct. 11, 2022. (Year: 2022).*

*Primary Examiner* — Scott J Medway
(74) *Attorney, Agent, or Firm* — Francis C. Hand; CARELLA, BYRNE, ET AL (57) ABSTRACT

In one embodiment, the dressing has a base which is to be adhered to a patient about a catheter site, an aperture in the base to pull a catheter line through and a cover with a window that is folded over and onto the base in a sealed manner. In another embodiment, the dressing has two covers with windows for folding over separate sections of a base to seal in the components of a catheter assembly with multiple catheters extending from a common housing.

14 Claims, 8 Drawing Sheets

(56) References Cited

U.S. PATENT DOCUMENTS

| | | | | |
|---|---|---|---|---|
| 4,417,710 A * | 11/1983 | Adair | A61G 15/16 248/205.2 |
| 4,449,975 A * | 5/1984 | Perry | A61M 25/02 128/877 |
| 4,517,971 A * | 5/1985 | Sorbonne | A61M 25/02 604/174 |
| 4,633,863 A * | 1/1987 | Filips | A61M 25/02 128/877 |
| 4,671,787 A * | 6/1987 | Widman | A61M 25/02 604/179 |
| 4,678,462 A * | 7/1987 | Vaillancourt | A61M 25/02 128/877 |
| 4,767,405 A * | 8/1988 | Lokken | A61M 25/02 604/164.08 |
| 4,846,807 A * | 7/1989 | Safadago | A61M 25/02 604/179 |
| 4,966,590 A * | 10/1990 | Kalt | A61M 25/02 128/DIG. 26 |
| 4,976,698 A * | 12/1990 | Stokley | A61M 25/02 604/174 |
| 5,383,893 A * | 1/1995 | Daneshvar | A61B 17/135 128/118.1 |
| 5,423,737 A * | 6/1995 | Cartmell | A61F 13/023 206/440 |
| 5,702,356 A * | 12/1997 | Hathman | A61F 13/0206 602/41 |
| 5,707,348 A * | 1/1998 | Krogh | A61M 25/02 602/41 |
| 5,820,578 A * | 10/1998 | Johansen | A61F 13/0203 602/41 |
| 5,885,254 A * | 3/1999 | Matyas | A61M 25/02 604/174 |
| 6,124,520 A * | 9/2000 | Roberts | A61F 13/0206 602/56 |
| 6,124,521 A * | 9/2000 | Roberts | A61M 25/02 602/56 |
| 6,841,715 B2 * | 1/2005 | Roberts | A61F 13/023 602/56 |
| 7,661,152 B2 * | 2/2010 | Manzano-Rivera | A61M 25/02 2/338 |
| 8,663,171 B2 * | 3/2014 | Tambourgi | A61M 25/02 604/174 |
| 9,554,946 B2 * | 1/2017 | Tang | A61M 25/02 |
| 9,572,942 B2 * | 2/2017 | Conrad-Vlasak | A61F 13/00 |
| 2004/0138602 A1 * | 7/2004 | Rossen | A61F 13/0226 602/41 |
| 2005/0020977 A1 * | 1/2005 | Eldridge | A61M 25/02 604/111 |
| 2005/0215953 A1 * | 9/2005 | Rossen | A61M 25/02 604/180 |
| 2006/0011501 A1 * | 1/2006 | Itou | A61M 25/002 206/370 |
| 2006/0211994 A1 * | 9/2006 | Roman | A61M 25/02 128/DIG. 26 |
| 2010/0198161 A1 * | 8/2010 | Propp | A61F 13/0269 604/180 |
| 2011/0098622 A1 * | 4/2011 | Hatanaka | A61F 13/0269 602/57 |
| 2013/0150796 A1 * | 6/2013 | Souza | A61M 25/02 604/180 |
| 2013/0317368 A1 * | 11/2013 | Warren | A61B 5/6801 600/473 |
| 2013/0317445 A1 * | 11/2013 | Steer | A61M 25/02 604/180 |
| 2014/0144798 A1 * | 5/2014 | Benesh | B65D 73/0021 206/363 |
| 2014/0188079 A1 * | 7/2014 | Simons | A61M 25/02 604/179 |
| 2014/0257242 A1 * | 9/2014 | Sung | A61M 25/02 156/289 |

* cited by examiner

DRESSING

This application is a continuation of U.S. Ser. No. 15/193,681, filed Jun. 27, 2016.

This invention relates to a dressing. More particularly, this invention relates to a dressing for protecting an indwelling catheter access site.

As is known, various catheters have been attached to patients for the infusion of pain drugs, chemotherapy, antibiotics, antiviral or antifungal drugs as well as for hydration and nutrition. In some cases, the catheters are required to remain in place for an extended period of time.

As described in U.S. Pat. Nos. 9,220,869 and 8,778,387, it is known to apply a dressing to a patient's skin to cover a catheter insertion site at which a catheter punctures a patient's skin.

As described in U.S. Pat. No. 6,998,511, dressings which cover catheters are generally known. The catheter may be inserted at a site on the patient and the site may be covered by the dressing. A window, or transparent film, may be provided within the dressing for viewing of the site.

As described in U.S. Pat. No. 7,812,212, it is known to provide a dressing for protecting a catheter access site as well as an implanted port at the site with a tube from the port extending from under the dressing.

It is known that medical tubing connected to indwelling catheters can be subjected to pulling forces caused by patient movement or by snagging of the tubing on other objects. These pulling forces might peel the dressing securing the tubing and/or catheter, infusion needle, etc. off of a patient's skin thereby exposing the catheter site, implanted port or an infusion needle. Also, this may weaken the adhesion between the dressing and the patient's skin, potentially exposing the catheter site to harmful bacteria. It is an object of the invention to provide a dressing for protecting a catheter site as well as a catheter extending from the site.

It is another object of the invention to provide a dressing for a catheter site that allows access to a catheter extending from the site.

It is another object of the invention to provide a dressing that maintains a catheter extending from a catheter site in a sealed condition when not in use and which allows ready access to the catheter when use is required.

It is another object of the invention to provide a dressing for a catheter site that can be easily applied to a patient and that is easy to manipulate to obtain access to a sealed in place catheter.

Briefly, the invention provides a dressing for a catheter site comprised of a base for adhering to a patient with an opening for passage of a catheter from the catheter site and a cover that can be folded over and secured to the base to close in the catheter and that can be peeled from the base to allow access to the catheter.

In one embodiment, the base of the dressing is made of a sheet of medical grade polyethylene and has an adhesive on an underside for adhering to a patient. The base also has an opening for passage of a catheter therethrough from the catheter site. In addition, a removable silicone release liner is disposed over the adhesive of the base. Upon use of the dressing, the release liner is manually removed, the dressing applied against the skin of a patient to encompass a catheter site and the catheter passed through the opening of the base.

The dressing may also have a pad disposed on the base over the opening therein for placement of a catheter thereon. To this end, the pad has a slit extending from one side thereof towards a central area thereof for passage of the line of the catheter therethrough. The line of the catheter may then be wound onto itself and placed on the pad.

In this embodiment, the cover is secured to the base for movement between an opened position spaced from the base and a closed position over the base and over the wound-up catheter line on the pad.

The cover has a window for viewing of the base and wound-up catheter line on the pad and a frame secured about a periphery of the window with an adhesive on an outer surface thereof for securement to the base. In addition, a removable silicone release liner is disposed over the adhesive of the frame.

The window is made of a breathable urethane with a preformed bubble for encompassing, i.e. fully encasing, a wound-up catheter line on the pad and a peripheral flange surrounding the bubble. One side of the flange is secured as by welding directly to the sheet of polyethylene of the base to form a unitary structure.

The frame is made of polyethylene and is of U-shape that is secured to three sides of the peripheral flange of the window in order to rigidify the perimeter of the urethane window for alignment over the base of the dressing.

Upon use of the dressing, after application of the base to a patient and placement of the catheter line on the pad, the release liner is manually removed from the frame of the cover and the cover folded over the base so that the U-shaped frame adheres to the base on three sides in a sealed manner with the window encompassing the wound-up catheter line on the pad. Since the window is secured to the base on the dressing is peeled away from the base while remaining hinged thereto to expose the catheter line. The drug or solution may then be administered into the catheter line in a conventional manner. After delivery, the cover may be reclosed on the base to again seal in the catheter line within the window.

Where a patient is "hooked" into an IV line or the like for an extended time and there is a need to "unhook" the patient, for example, to take a shower, the cover which is in the opened position while the patient is "hooked in" is folded over the base into the closed position to protect the catheter line during the shower.

The window of the dressing and the opening in the base allows medical personnel to view the catheter site from time to time.

In another embodiment, the dressing is made for use with a catheter site having a catheter assembly with multiple catheters extending from a common housing which, in turn, is connected via a single line to the catheter site.

In this embodiment, the base has a pair of sections defining an L-shape with an opening disposed in one of the sections and with the cover extending from this section. The base also has a slit extending from the opening to an edge of the base for passage of a catheter line of the catheter assembly. This embodiment is particularly useful for Peripherally Inserted Central Catheters known as PICCs.

The base is made of a sheet of medical grade polyethylene with an adhesive on an underside for adhering to a patient and a removable silicone release liner disposed over the adhesive.

The cover is made as in the first embodiment with a window and a frame secured about a periphery of the window with an adhesive on an outer surface for securement to the base and a removable silicone release liner disposed over the adhesive.

Upon use of the dressing, the release liner is manually removed from the base and the dressing applied against the skin of a patient to encompass the catheter site and the line of the catheter assembly passed through the slit in the base and into the opening of the base. The release liner is then manually removed from the frame of the cover and the cover folded over the base so that the U-shaped frame adheres to the base on three sides in a sealed manner with the window encompassing the common housing of the catheter assembly. The multiple catheters of the assembly are then laid over the second section of the base.

This embodiment also has a second cover of like construction but a longer length secured to the second section of the base for folding over the multiple catheters. Upon use, after placement of the multiple catheters on the second section of the base, the release liner of the second cover is removed and the cover folded over and adhered to the base to place the window of the cover over the multiple catheters. At the same time, the frame of the cover seals against the base as well as overlying one side of the first cover in sealed relation.

The dressing of each embodiment may be made so that base has an enlarged portion at one corner and the cover(s) has a tab for disposition over and within the enlarged portion in closed position of the cover. This facilitates opening of the cover(s) away for the base without risk of pulling the base from adhesion to a patient.

These and other objects and advantages of the invention will become more apparent from the following description taken in conjunction with the drawings wherein.

Figure 1:
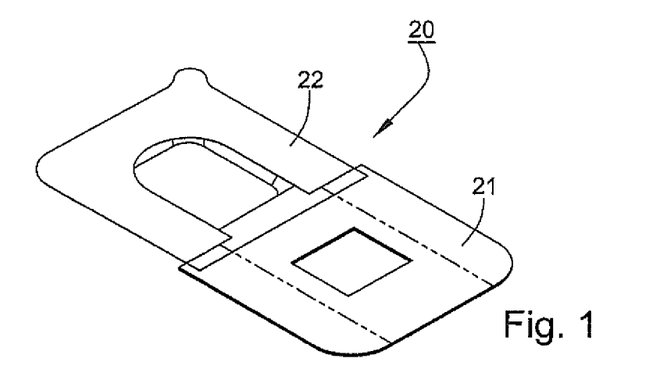
FIG. 1 illustrates a top view of a dressing made with a base and a cover in accordance with the invention.

Referring to FIG. 1, the dressing 20 comprises a base 21 and a cover 22 for movement between an opened position spaced from the base 20 and a closed position over the base 21.

Figure 2:
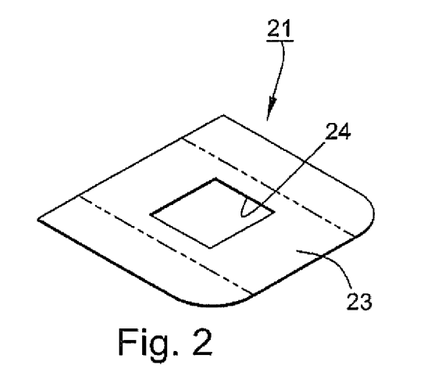
FIG. 2 illustrates a top view of the base of the dressing of FIG. 1.
Figure 6:
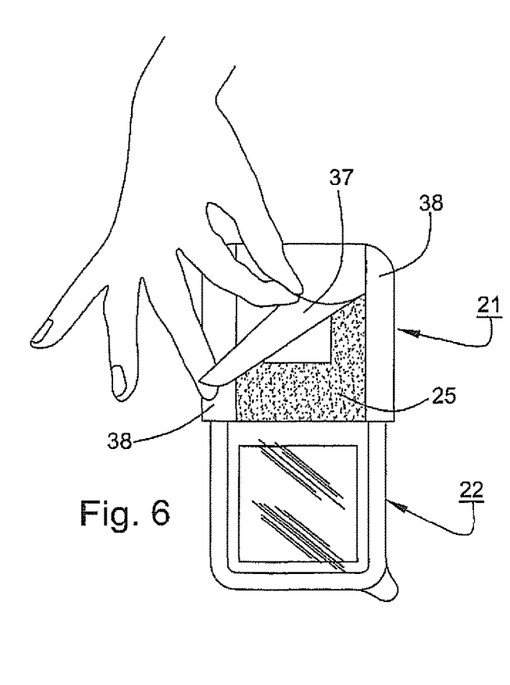
FIG. 6 illustrates a view of the dressing of FIG. 1 during application to a patient.

Referring to FIGS. 2 and 6, the base 21 is made of a sheet 23 of medical grade polyethylene of generally square or rectangular shape with a centrally located opening 24 and has an adhesive 25 on an underside for adhering to a patient. For example, the base 21 is a single coated polyethylene tape 3M-1521.

In addition, the base 21 has a silicone coated release liner 26, such as, a 3M 1361, disposed over the adhesive 25 of the sheet 23.

Figure 3:
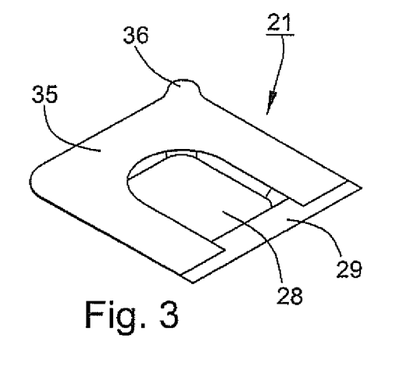
FIG. 3 illustrates a top view of the cover of FIG. 1.
Figure 4:
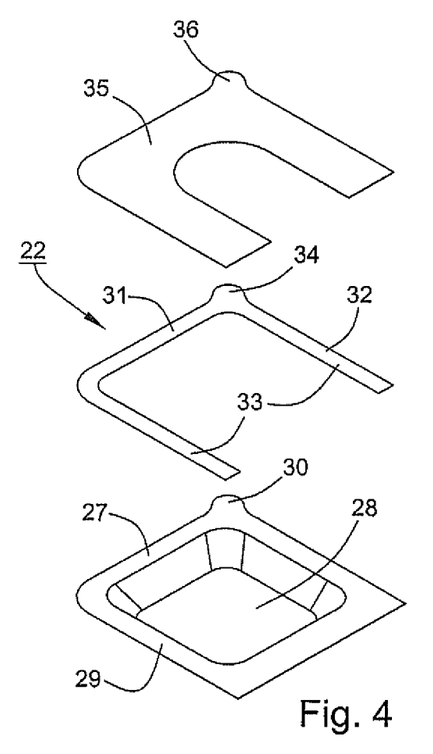
FIG. 4 illustrates an exploded view of the cover of FIG. 3.

Referring to FIGS. 3 and 4, the cover 22 has a preformed transparent window 27 made of a breathable urethane of a thickness of 2.5 mil with a preformed bubble 28 and a peripheral flange 29 surrounding the bubble 28.

As illustrated in FIG. 4, one side of the flange 29 is wider than the remaining three sides of the flange 29 for securement, as by welding, directly to the sheet 23 of polyethylene of the base 21 as illustrated in FIG. 1 to form a unitary structure. In addition, one corner of the flange 29 is formed as an outwardly projecting tab 30.

The cover 22 also has a U-shaped frame 31 secured to the flange 29 about three sides of the periphery of the window 27 with an adhesive 32 on an outer surface thereof for securement to the base 21. For example, the frame 31 is made of a single coated polyethylene tape, e.g. a 3M 9860, of approximately 0.020 inches thick to provide stability to the window 27.

As illustrated in FIG. 4, the frame 31 includes a pair of parallel legs 33 that extend over only a portion of the wider side of the flange 29 to be in abutment with a side of the sheet 23 when the dressing 20 is assembled. (See FIG. 1). The uncovered portion of this side of the flange 29 thus forms a "hinge" for folding of the cover 22 onto and from the base 21.

The frame 31 also has a corner that is formed as an outwardly projecting tab 34 that overlies the tab 30 of the window 27.

In addition, the cover 22 has a silicone coated release liner 35, such as, a Kraft Liner 3M 9968, disposed over the adhesive 32 of the frame 31. This liner 35 also has a corner that is formed as an outwardly projecting tab 36 that overlies the tab 30 of the window 27 and the tab 34 of the frame 31.

Figure 5:
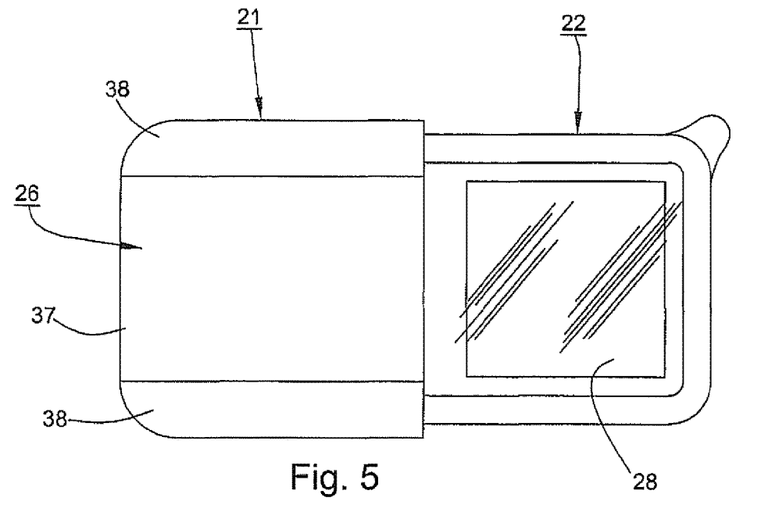
FIG. 5 illustrates a bottom view of the dressing of FIG. 4.

Referring to FIGS. 5 and 6, the release liner 26 of the base 21 is formed of three sections, namely a rectangular central section 37 that is to be first removed when applying the dressing 20 to a patient and two side sections 38 that are to remain in place during initial placement of the dressing 20 on a patient. The two side sections 38 allow a user to apply the dressing 20 to a patient without needing to touch the adhesive 25 on the sheet 23.

Referring to FIG. 6, in order to apply the dressing 20 to a catheter site, the central section 37 of the release liner 26 on the base 21 is removed.

Figures 7, 8, 9:
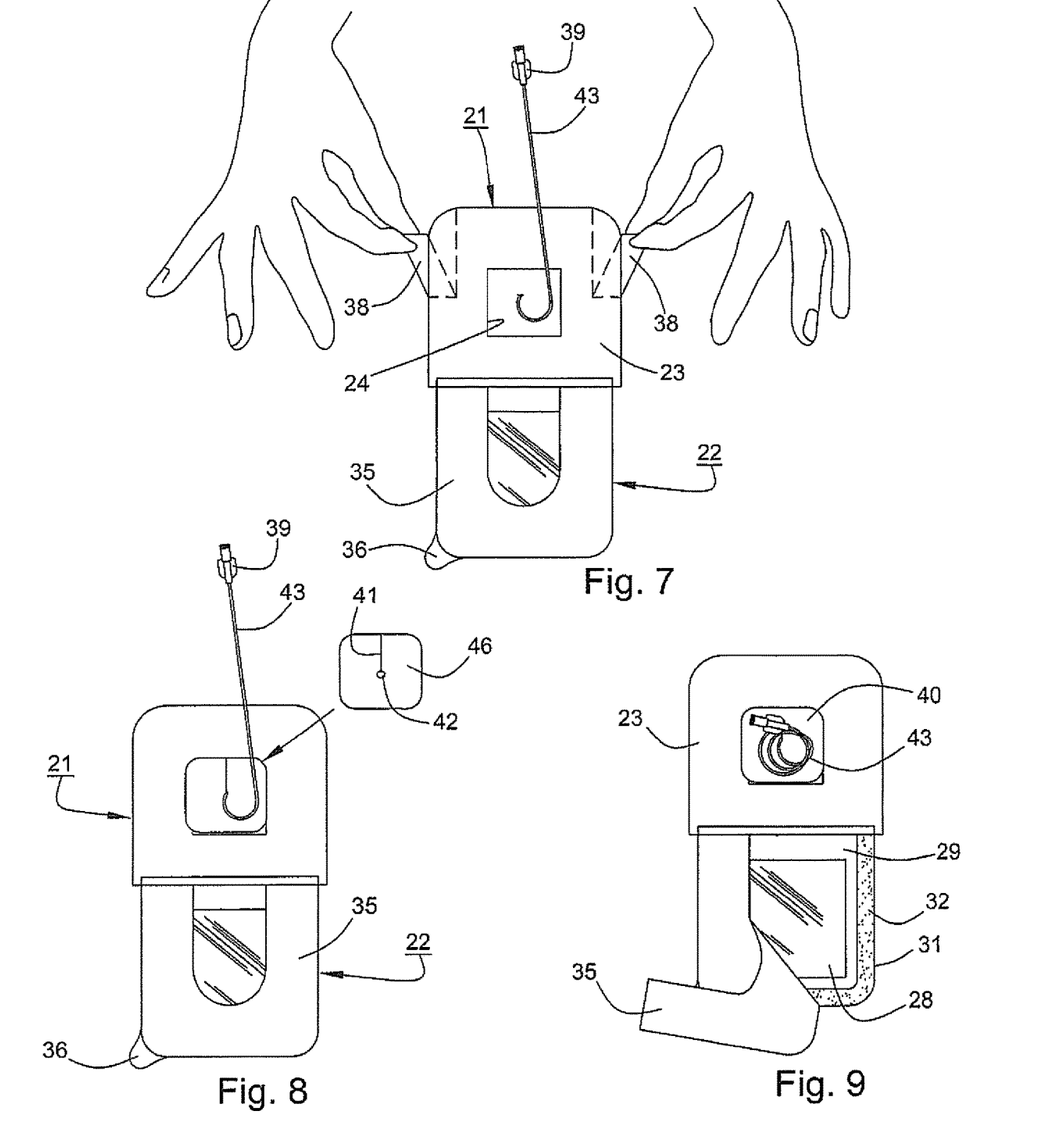
FIG. 7 illustrates a view of the dressing of FIG. 4 applied to a catheter site with a catheter line extending through an opening in the base.
FIG. 8 illustrates a view of the dressing of FIG. 4 with a pad on the base.
FIG. 9 illustrates a view of a coiled catheter line on the pad on the base in accordance with the invention.

Referring to FIG. 7, the dressing 20 is then placed over the catheter site and the catheter 39 at the catheter site is pulled through the opening 24 in the sheet 23, the remaining side sections 38 are then removed and the base 21 is adhered to the patient (not shown).

Referring to FIG. 8, a soft foam comfort pad 40 may be disposed on the base 21 over the opening 24 for placement of the catheter 39 thereon. As illustrated, the pad 40 has a slit 41 extending from one side thereof to a centrally located aperture 42 for passage of a catheter line 43 of the catheter 39 therethrough to the aperture 42.

Referring to FIG. 9, after winding up of the catheter line 43 of the catheter 39 and placement on the pad 40, the release liner 35 on the cover 22 is removed to expose the adhesive 32 and the cover 22 folded over the base 21 and pressed down on three sides.

Figure 10:
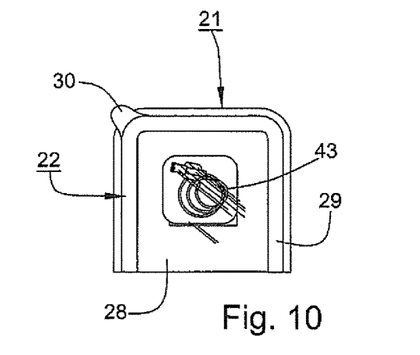
FIG. 10 illustrates a view of the dressing of FIG. 4 with the cover folded over the base.

Referring to FIG. 10, after folding onto the base 21, the cover 22 seals against three sides of the base 21 via the adhesive 32 while the fourth side of the base 21 is closed by the flange 29 of the window 27. At this time, the coiled catheter line 43 is encompassed by the window 27 of the cover 22 and may be readily viewed. As viewed, the bubble 28 is positioned over and fully encases the catheter 39 and catheter line 43.

Figure 11:
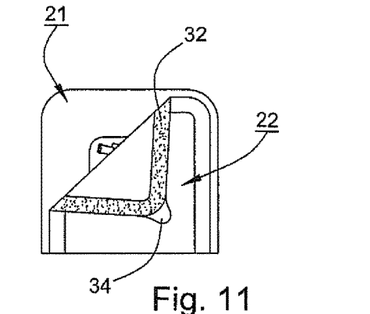
FIG. 11 illustrates a view of the dressing of FIG. 4 during unpeeling of the cover from the base.

Referring to FIG. 11, in order to uncover the catheter line 43, the overlying tabs 30 (34) are manually grasped and the cover 22 peeled back from the base 21. After servicing, the catheter line 43 is again coiled onto the pad 40 and the cover 22 folded back onto the base 21 to enclose the catheter line 43.

In order to administer a drug, or solution or the like to a patient, the cover 22 of the dressing 20 is peeled away from the base 21 while remaining hinged thereto to expose the catheter line 43. The drug or solution may then be administered into the catheter line 43 in a conventional manner. After delivery, the cover 22 may be reclosed on the base 21 to again seal in the catheter line 43 within the window 27.

Where a patient is "hooked" into an IV line or the like for an extended time and there is a need to "unhook" the patient, for example, to take a shower, the cover 22 which is in the opened position while the patient is "hooked in" is folded over the base 21 into the closed position to protect the catheter line 43 during the shower.

Figure 12:
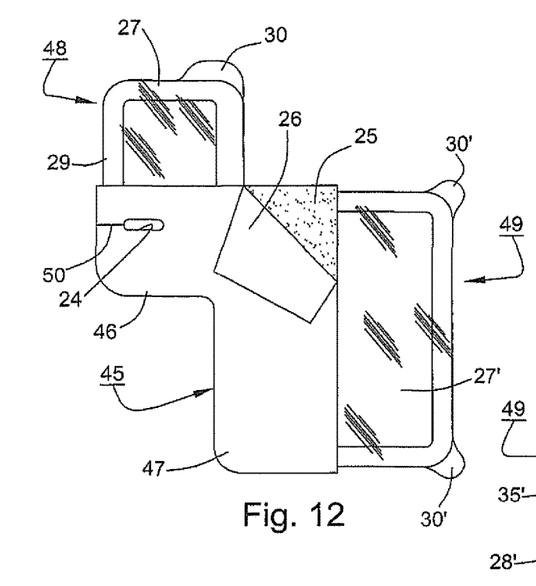
FIG. 12 illustrates a bottom view of a dressing in accordance with a second embodiment of the invention.
Figure 13:
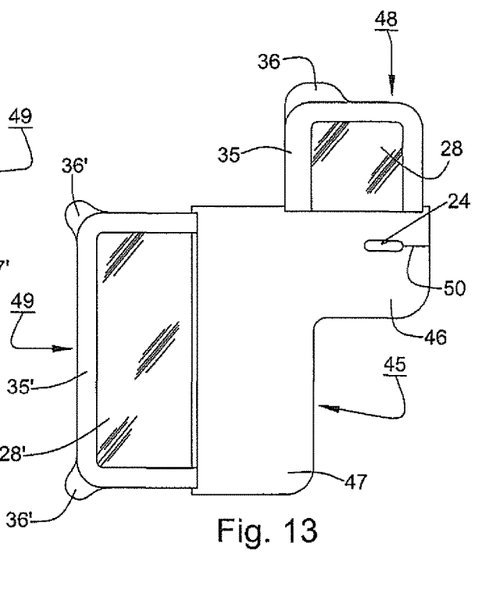
FIG. 13 illustrates a top view of the dressing of FIG. 12.

Referring to FIGS. 12 and 13, wherein like reference characters indicate like parts as above, in another embodiment, the dressing 44 includes a base 45 of L-shape defining two sections 46, 47 with a first cover 48 secured to one section 46 of the base 45 and a second cover 49 secured to the other section 47 of the base 44.

The base 45 is made of a sheet 23 of medical grade polyethylene with an opening 24 and has an adhesive 25 on an underside for adhering to a patient. In addition, the base 45 has a silicone coated release liner 26, as above, disposed over the adhesive 25 of the sheet 23.

The section 46 to which the first cover 48 is secured has a slit 50 extending from the opening 24 to an edge of the base 45 for passage of a catheter line therethrough to the opening.

The first cover 48 is made in a similar manner to the cover 22 described above with respect to FIG. 4 having a preformed transparent window 27 with a peripheral flange 29 about a bubble 28 and an outwardly projecting tab 30 on the flange 29, a U-shaped frame 31 secured about three sides of the periphery of the window 27 with an adhesive 32 (see FIG. 16) on an outer surface thereof for securement to the base 45 and a removable release liner 35 over the adhesive 32 on the frame 31.

The frame 31 also has a corner that is formed as an outwardly projecting tab (not shown) that overlies the tab 30 (see FIG. 12) of the window 27.

In addition, the liner 35 also has a corner that is formed as an outwardly projecting tab 36 (FIG. 12) that overlies the tab 30 (FIG. 11) of the window 27 and the tab of the frame 31.

The second cover 49 is similar to the first cover 48 having a preformed transparent window 27' of medical grade plastic with a peripheral flange 29' about a bubble 28', a U-shaped frame 31' secured about three sides of the periphery of the window 27' with an adhesive 32 (see FIG. 19) on an outer surface thereof for securement to the base 45 and a removable release liner 35' over the adhesive 32 on the frame 31'.

The second cover 49 is of an elongated rectangular shape and the window 27' has a pair of outwardly projecting tabs 30' at two corners of the flange 29'.

The frame 31' also has a pair of outwardly projecting tabs (not shown) at two corners that overlie the tabs 30' of the window 27'.

In addition, the liner 35' also has a pair of outwardly projecting tabs 36 at two corners that overlie the tabs of the window 27' and the tabs 30' of the frame 31'.

Figure 14:
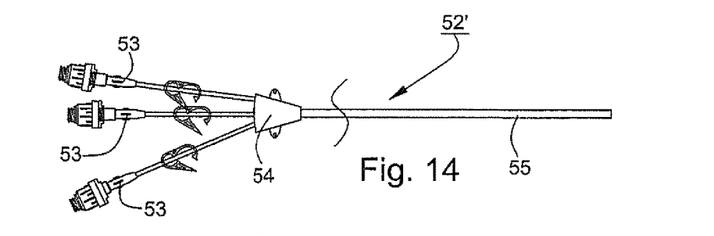
FIG. 14 illustrates a partial view of a catheter assembly with multiple catheters extending from a common housing.

Referring to FIG. 14, the catheter assembly 52 has multiple catheters 53 extending from a common housing 54 which, in turn, is connected via a single line 55 to a catheter site (not shown).

Figure 15:
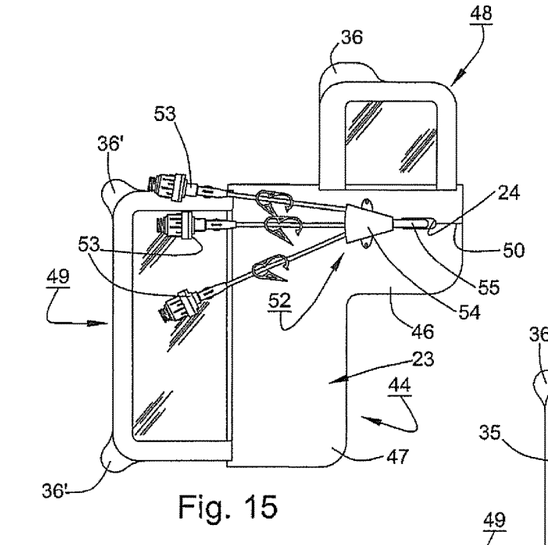
FIG. 15 illustrates a view of the dressing of FIGS. 12 and 13 during initial placement over the catheter assembly of FIG. 14.

Referring to FIG. 15, in use, the dressing 44 is constructed to protect the catheter assembly 52 at a catheter site, for example, on the arm of a patient.

As above, in order to apply the dressing 44 to a catheter site, the release liner 26 on the base 45 is removed (see FIG. 12), the dressing 44 is placed over the catheter site and the catheter line 55 from the catheter site is pulled through the slit 50 to the opening 24 in the first section 46 of the sheet 23. At this time, the housing 54 is laid on the section 46 and the multiple catheters 53 laid across the section 46.

Figure 16:
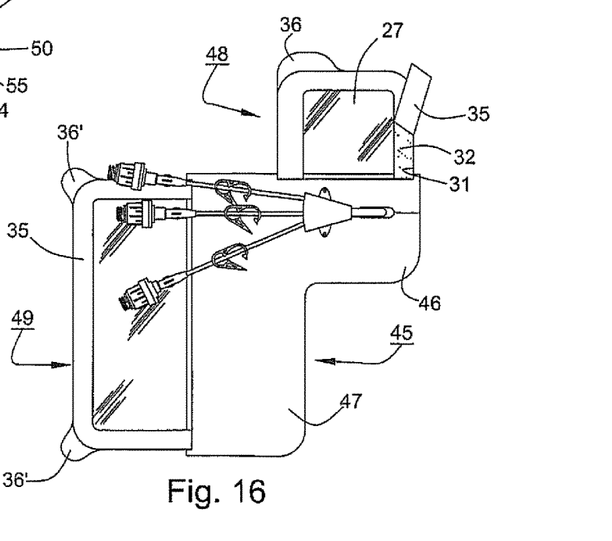
FIG. 16 illustrates a top view of the dressing of FIG. 12 prior to folding over of the first cover.

Next, as indicated in FIG. 16, the release liner 35 on the cover 48 is removed to expose the adhesive 32 on the frame 31' and the cover 48 folded over the base 45 and pressed down on three sides.

Figures 17, 18:
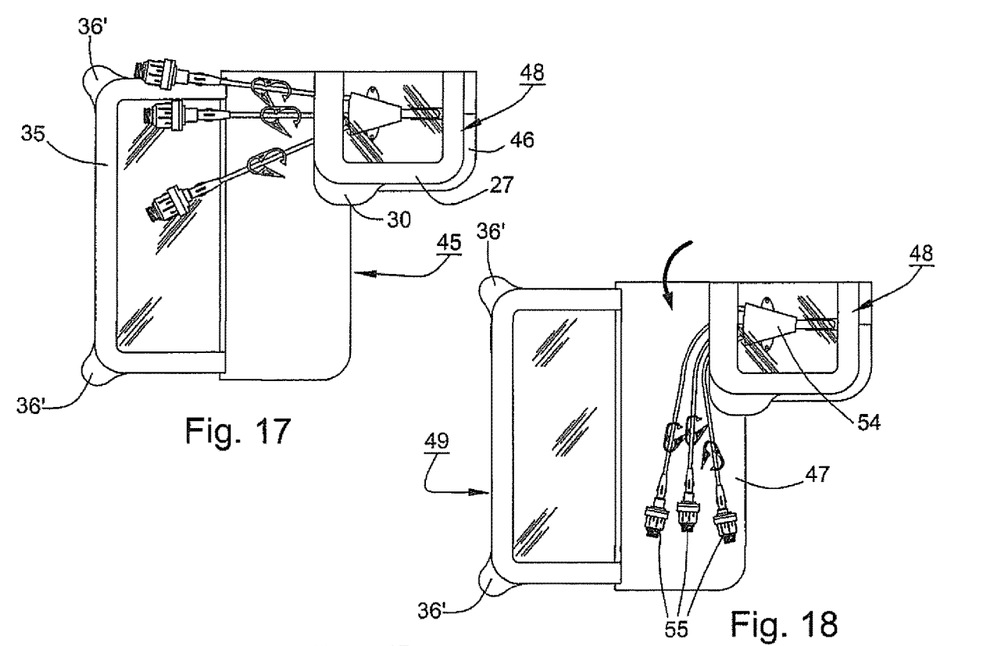
FIG. 17 illustrates a top view of the dressing of FIG. 12 after folding over of the first cover.
FIG. 18 illustrates a top view of the dressing of FIG. 12 after placement of the multiple catheters over the base and prior to folding over of the second cover.

Referring to FIG. 17, after folding onto the base 45, the cover 48 seals against two sides of the base section 46 via the adhesive 32 on the frame 31' and over the multiple catheters 53 onto the base section 46. As illustrated, the flange 29 wider on side that holds the lines of the catheters 53 in place. The wider flange increases the adhesive surface area and makes the flange stronger and holds the catheters more securely in place.

As illustrated, the cover 48 is of a length approximately equal to the width of the section 46 of the sheet 23 of the base 45. Thus, the overlying tabs of the frame 31' and the window 27' project beyond the base section 46.

Figure 19:
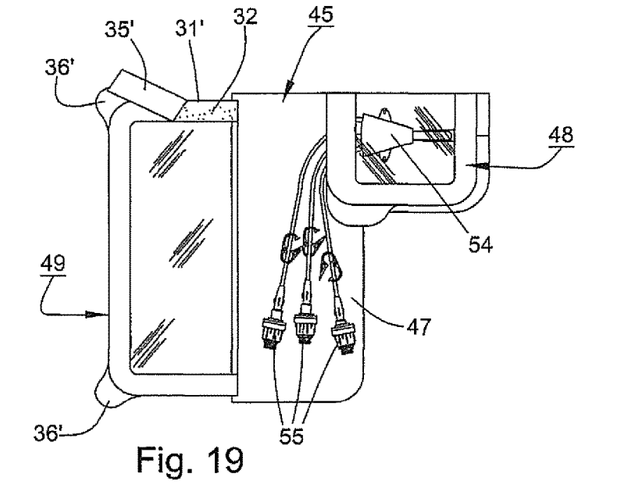
FIG. 19 illustrates a top view of the dressing of FIG. 12 during removal of the release liner and prior to folding over of the second cover.

Referring to FIGS. 18 and 19, thereafter, the multiple catheters 55 are laid over the second section 47 of the sheet 23 of the base 45 and the release liner 35' removed from the frame 31' of the second cover 49 to expose the adhesive 32 thereon. Next, the second cover 49 is folded over the multiple catheters 55 to seal against the second section 47 of the sheet 23 of the base 45.

Figure 20:
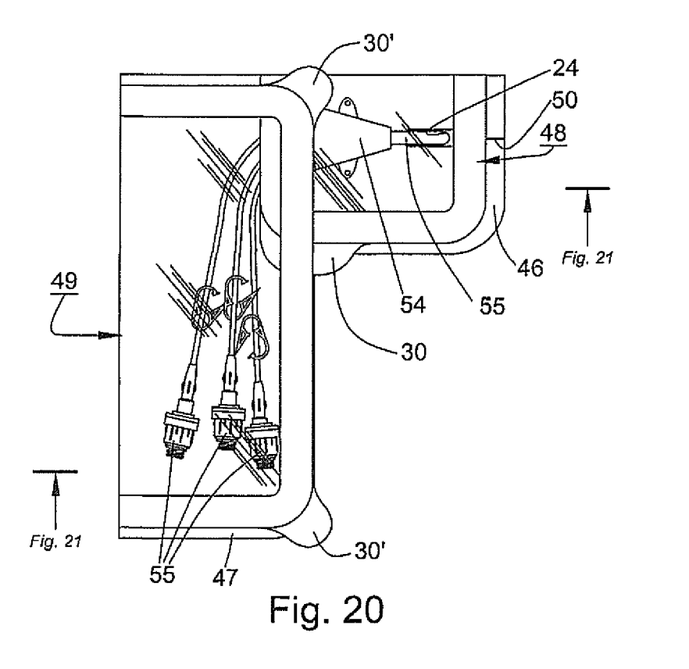
FIG. 20 illustrates a top view of the dressing of FIG. 12 after folding over of the second cover.
Figure 21:
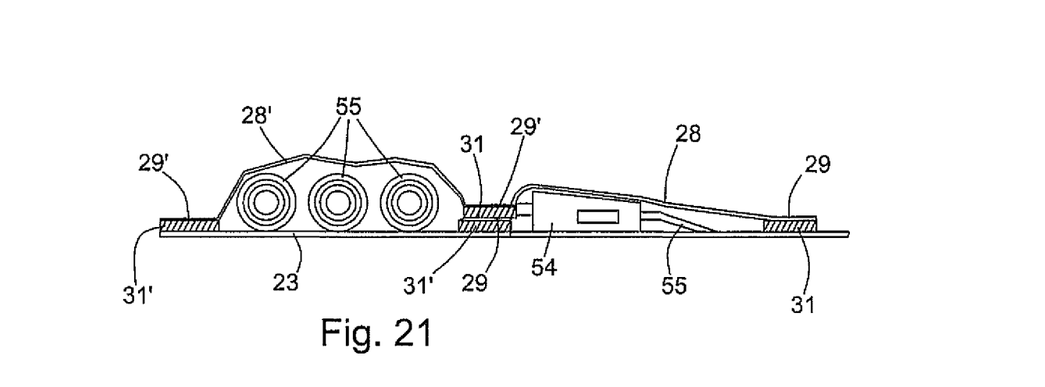
FIG. 21 illustrates a part cross-sectional view taken on line 21-21 of FIG. 20.

As illustrated in FIGS. 20 and 21, the frame 31' not only seals against the second section 47 of the base 45 but also over the side of the first cover 48 covering the multiple catheters 55 to seal any openings therebetween. In addition, the tabs 30' of the window 27' extends outwardly of the base 45.

Should a need arise to gain access to the catheters 55, the second cover 49 is peeled away from the closed position of FIG. 20 to an opened position such as shown in FIG. 19. Thereafter, the second cover 49 is again pressed onto the base 45 to seal the catheters 55 from the surrounding environment.

Similarly, should a need arise to gain access to the housing 54, both covers 48, 49 are peeled away to opened positions.

Figure 22:
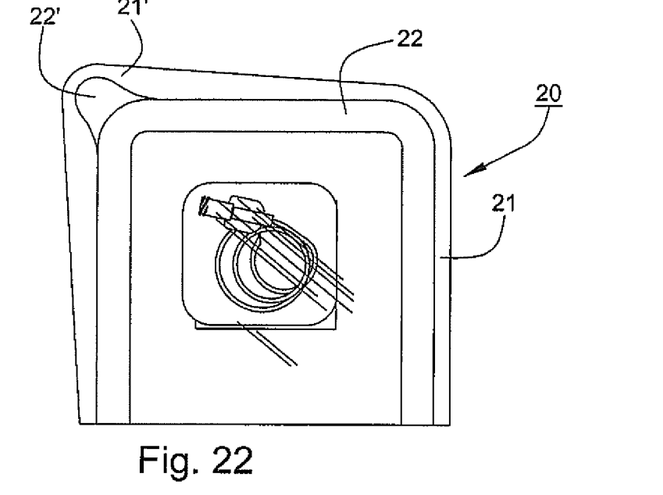
FIG. 22 illustrates a view of a dressing similar to FIG. 10 with a base having an enlarged portion to receive a tab of the cover.
Figure 23:
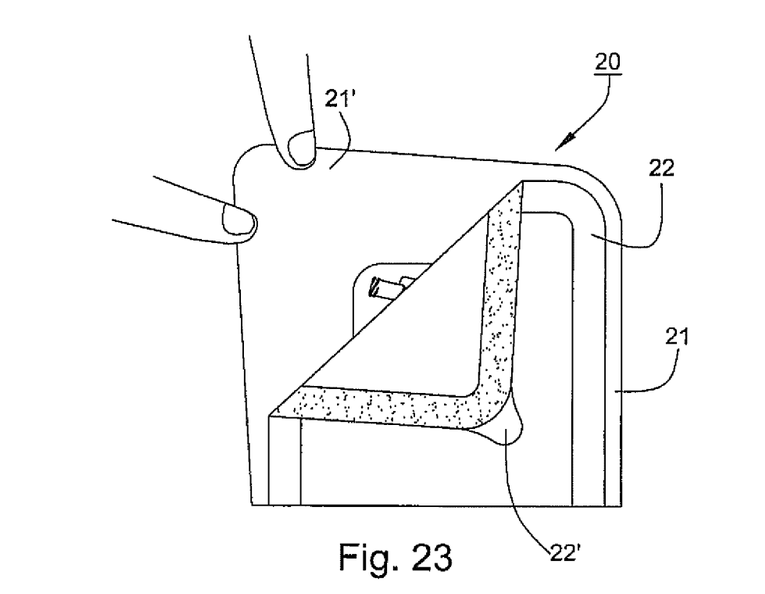
FIG. 23 schematically illustrates the dressing of FIG. 22 during opening of a cover.

Referring to FIGS. 22 and 23 wherein like reference characters indicate like parts as above, the dressing 20 may be made with a base 21 having an enlarged portion 21' at one corner thereof and with the cover 22 having a tab 22' for disposition over and within the enlarged portion 21' in closed position (FIG. 22). The tab 22' is releasably secured to the enlarged portion 21' to remain flat and secure. In order to open the dressing 20, the tab 22' is peeled back from the base 21 (FIG. 23) while the user holds the enlarged portion 21' down against the patient. Thus, the cover 22 may be peeled away for the base 21 without risk of pulling the base from adhesion to a patient.

The embodiment of FIGS. 12 to 21 may be made with similar tabs. For example, one section 46 of the base 45 may have an enlarged portion at one corner and the first cover 48 would have a tab for disposition over and within enlarged portion in the closed position thereof. The other section 47 of the base 45 would have an enlarged portion at the corner where the tab 30' of the window 27' and tab 36' of the frame 35' overlie the base section 47.

The invention thus provides a dressing that maintains a catheter extending from a catheter site in a sealed condition when not in use and which allows ready access to the catheter when use is required. Further, the invention provides a dressing that can be easily applied to a patient, that is easy to manipulate to obtain access to a sealed in place catheter and that protects a catheter site as well as a catheter extending from the site.

What is claimed is:

1. A dressing for a catheter site comprising
    a base having an adhesive on an underside thereof for adhering to a patient and an opening for passage of a catheter therethrough from the catheter site; and
    a cover secured to said base for movement between an opened position spaced from said base and a closed position over said base, said cover having a window with a preformed bubble for positioning over and fully encasing a catheter on said base and a frame secured about a periphery of said window with an adhesive on an outer surface thereof for securement to said base to maintain the catheter in a sealed condition.

2. A dressing as set forth in claim 1 wherein said opening in said base is located centrally of said base and said window of said cover is located centrally of said cover.

3. A dressing as set forth in claim 1 further comprising a foam pad disposed on said base over said opening therein for placement of a catheter thereon, said pad having a slit extending from one side thereof towards a central area thereof for passage of a catheter line therethrough.

4. A dressing as set forth in claim 1 wherein said frame of said cover has an outwardly extending tab at one corner thereof for manual peeling of said cover from said base from said closed position to said opened position.

5. A dressing as set forth in claim 1 wherein said base is made of a medical grade polyethylene, said frame of said cover is made of medical grade polyethylene and said window is made of polyurethane.

6. A dressing as set forth in claim 1 further comprising a removable silicone release liner over said adhesive of said frame.

7. A dressing as set forth in claim 1 further comprising a removable silicone release liner over said adhesive of said base.

8. A dressing as set forth in claim 1 wherein said adhesive of said cover is peelable from said base.

9. A dressing as set forth in claim 1 wherein said window is made of a breathable urethane.

10. A dressing as set forth in claim 1 wherein said base has a slit extending from said opening to an edge of said base for passage of a catheter line therethrough.

11. A dressing as set forth in claim 1 wherein said base has an enlarged portion at one corner thereof and said cover has a tab for disposition over and within said enlarged portion in said closed position.

12. A dressing for a catheter site comprising
    a base having an adhesive on an underside thereof for adhering to patient and an opening for passage of a catheter having a catheter line extending from the catheter site; and
    a cover secured to said base for movement between an opened position spaced from said base and a closed position over said base, said cover having a window with a preformed bubble for positioning over and fully encasing a catheter and wound up catheter line on said base and a frame secured about a periphery of said window with an adhesive on an outer surface thereof for securement to said base to seal the catheter and catheter line therein.

13. A dressing as set forth in claim 12 further comprising a foam pad disposed on said base over said opening therein for placement of a catheter thereon, said pad having a slit extending from one side thereof towards a central area thereof for passage of a catheter line therethrough.

14. A dressing for a catheter site consisting essentially of
    a base having an adhesive on an underside thereof for adhering to a patient and an opening for passage of a catheter and catheter line therethrough from the catheter site; and
    a cover secured to said base for movement between an opened position spaced from said base and a closed position over said base, said cover having a window with a preformed bubble for positioning over and fully encasing a catheter and catheter line on said base and a frame secured about a periphery of said window with an adhesive on an outer surface thereof for securement to said base to maintain the catheter and catheter line in a sealed condition.

* * * * *